United States Patent [19]

Jelly

[11] Patent Number: Plant 5,634

[45] Date of Patent: Jan. 14, 1986

[54] ROSE PLANT NAMED JELROCAMI

[75] Inventor: Robert G. Jelly, Richmond, Ind.

[73] Assignee: E. G. Hill Co., Inc., Richmond, Ind.

[21] Appl. No.: 609,782

[22] Filed: May 14, 1984

[51] Int. Cl.[4] ..... A01H 5/00

[52] U.S. Cl. ..... Plt./20

[58] Field of Search ..... Plt./20

*Primary Examiner*—Robert E. Bagwill

*Attorney, Agent, or Firm*—Charles W. Rummler

[57] ABSTRACT

A new and distinct variety of rose plant of the tea class distinguished by its large, double red flowers which are borne on rigid and very long stems, the flowers when fully blown having a current red coloration on the inner surfaces of the petals and a crimson purple coloration on the outer surface of the petals. The flowers are long lasting as cut flowers and the petals drop off cleanly.

18 Drawing Figures

BACKGROUND OF THE NEW PLANT

This new rose plant was originated at Richmond, Ind., as a seedling resulting from my crossing of two carefully chosen rose plant varieties with the object of producing a new, double red tea class flower of an original scarlet red color borne on strong, very long stems, the plant to have a vigorous growth habit well adapted to forcing, especially in the summer. After careful study of the seedlings produced by this crossing, the seedling parent of my new rose variety was selected and propagated by bud grafting through several successive generations at Richmond, Ind., which demonstrated that the novel characteristics of the selected parent were fully retained from generation to generation and appeared to be firmly fixed. Plants of this new rose variety are now being grown at Richmond, Ind., and grown commercially for the European market at Antibes, France.

DESCRIPTION OF THE DRAWING

My new variety of rose plant is illustrated by the accompanying photographic drawing showing in full color the distinctive elements of the new plant and in which.

DESCRIPTION OF THE NEW PLANT

Figures 1, 2, 3, 4, 5, 6, 7, 8, 9, 10, 11, 12, 13, 14, 15, 16, 17, 18:
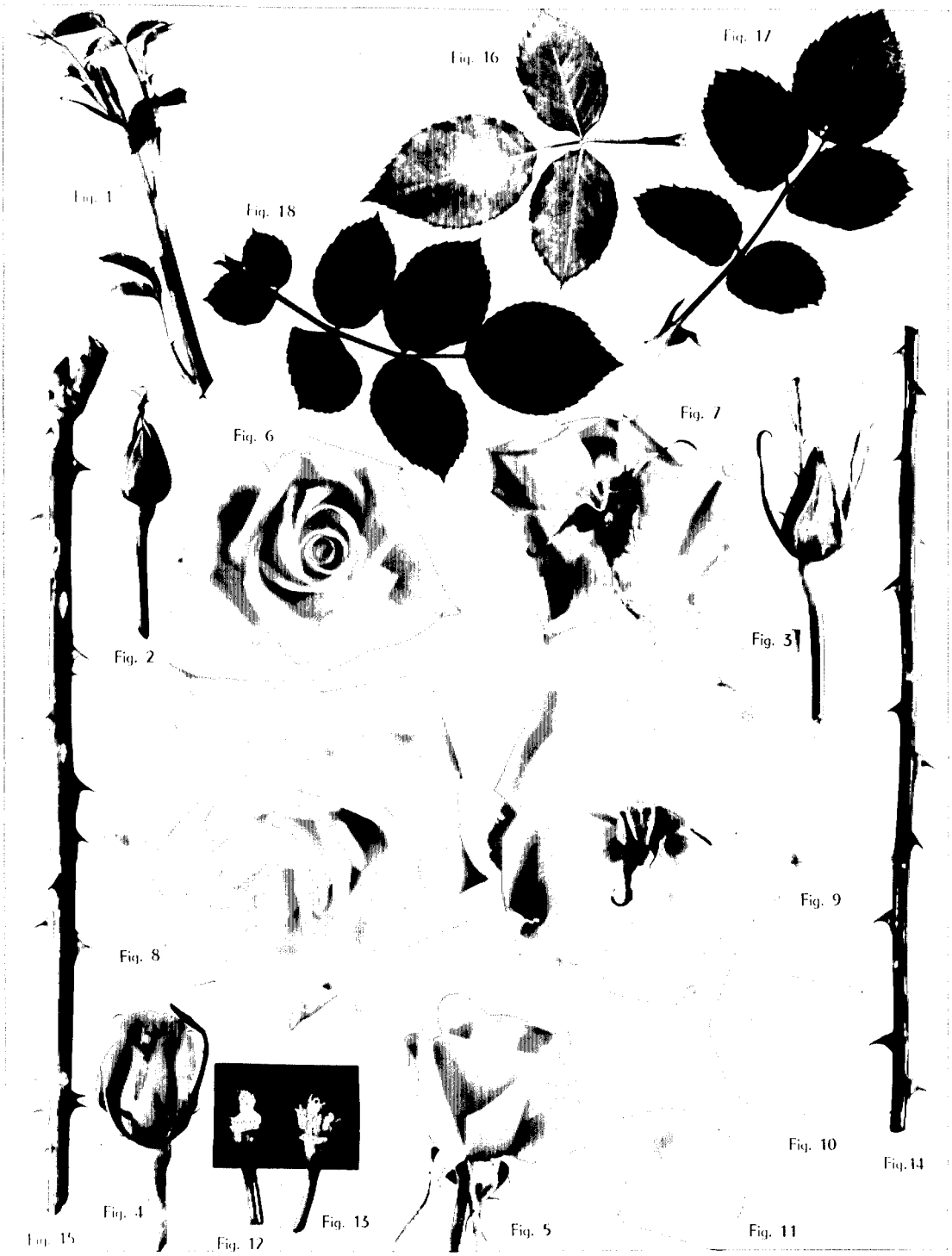
FIG. 1 shows a specimen of a young shoot.
FIG. 2 shows a specimen of the bud before the sepals open.
FIG. 3 is a specimen of the bud when the sepals have just opened.
FIG. 4 shows a specimen of bud at the opening of petals.
FIG. 5 shows a flower at the start of blowing.
FIG. 6 is a face view of a flower in the course of blowing.
FIG. 7 is a back or stem side view of a flower in the course of blowing.
FIG. 8 is a full face view of a flower at the end of blowing.
FIG. 9 is a back side view of a flower at the end of blowing.
FIG. 10 is a view showing the inner surface of a petal.
FIG. 11 is a view showing the outer or reverse side of a petal.
FIG. 12 is a view of a receptacle showing the disposition of the pistils (sepals, petals and stamens being removed)
FIG. 13 is a view of a receptacle showing the disposition of the stamens (the sepals and petals being removed)
FIG. 14 shows a portion of matured wood (main branch)
FIG. 15 shows a specimen of young wood.
FIG. 16 shows the outer or rear surface of a leaf having three leaflets.
FIG. 17 shows the inner or upper side surface of a leaf with five leaflets.
FIG. 18 shows the upper surface of a leaf having nine leaflets.

The following is a detailed description of my new rose plant as observed on plants being grown at Antibes, France, the color designations being according to The R.H.S. Colour Chart of The Royal Horticultural Society at London, England.

THE PLANT

Origin: Seedling.

Parentage:

*Seed parent.*—A selected rose plant of an unnamed variety of unknown origin.

*Pollen parent.*—The rose variety known as "Meger/Baccara" (R).

Classification:

*Botanic.*—Hybrid Tea Rose.

Form: An erect bush.

Height: In general, usually up to about 120 cm. As a result of cutting back of the plants to approximately 85 cm., the length of the flower stems in general are about 70 to 120 cm. long.

Growth: Vigorous and upright.

Branching: Normal.

Young stems:

*Color.*—Light Green 146B largely smudged with Reddish Brown.

Mature wood:

*Color.*—Bronze Green 146A slighly smudged with Reddish Brown.

Prickles:

*Shape.*—Upper edge — Straight slightly fringed, inflexed towards the base. Lower edge — Concave.

*Size.*—Large.

*Quantity.*—Medium.

*Color.*—On young stems — Reddish. On mature wood — Pinkish then Havana.

Foliage:

*Quantity.*—Abundant.

*Form of leaf.*—Odd pinnate.

*Leaflets.*—Number: 3, 5 and 7, more often 5. Shape: Oval with rounded apex and narrower and symmetrical margins, serrated, regular and simple. Texture: Leathery Color: Young Foliage: Upper surface — BronzeGreen 146A. Outer surface — Medium Green 148B largely smudged with Reddish Brown. Mature Foliage: Upper surface — Dark Green 147A. Bottom surface — Medium Green 147B.

*Stipules.*—Adnate, pectinate, fairly large and linear.

*Petiole.*—Inner surface — Grooved, Reddish Brown on young leaves becoming Medium Green on adult foliage. Outer surface — Light Green and bearing a few small hooked prickles.

THE BUD

Size: Medium.

Shape: Conical before opening of petals.

Length: 3.5 cm. on average outside the calyx and on opening of sepals.

Color of petals: On opening:

*Inner surface.*—Vermillion Red.

*Outer surface.*—Officer Red 45A; more and more flushed Cardinal Red 53A toward the base; more or less smudged blackish on outer petals.

Sepals:

*Inner surface.*—Tomentous, greenish.

*Outer surface.*—Light Green more or less smudged reddish, the outer sepals having their edges slightly appendiculated.

*Character.*—Sepals turn outwardly and downwardly at the start of blowing.

Peduncle:

*Length.*—12 cm. on average.

*Character.*—Straight, rigid, slighly smudged reddish brown. The peduncle is slightly glandular and sometimes bears a few small hooked prickles.

THE FLOWER

Size of bloom: Large.

*Diameter.*—12 cm. on average.

Shape: Parallel sides on start of blowing, then opening in hollow cup chorisis; double.

Petalage:

*Number.*—30 on average.

*Arrangement.*—Imbricated.

*Form.*—Wide fan-shaped with entire margins. The unguis is whitish on both sides.

*Texture.*—Firm.

*Color.*—On opening: Inner surface — Vermillion Red 44A. Outer surface — Vinous Pink 50A. In course of blowing: Inner surface — Surface Red 43B in center, very slightly flushed with Light Scarlet Red 43C at edge of petals. Outer surface 13 Crimson Purple 52A in center of petals and Vinous Red 50A at edge of petals. At end of blowing: Inner surface — Currant Red 47B. Outer surface — Crimson Purple 52A.

Fragrance: Nil.

Persistence: The petals drop off cleanly.

Resistance to diseases: Very good as observed where grown in France.

Lasting quality: As cut flowers, a relatively long time.

REPRODUCTIVE ORGANS

Stamens:

*Number.*—120 on average.

*Anthers.*—Normal, fuchsine.

*Filaments.*—Yellow at base, fuchsine, and irregular in height.

Pistils:

*Number.*—75 on average.

*Styles.*—Free, slightly twisted and of irregular height.

*Stigmas.*—Yellowish, largely shadowed with fuchsine.

This new variety of rose plant produces large, elegant flowers, particularly in bud, and when fully blown results in a double flower of scarlet red color in the center, slightly lighter on the edge of the inner surface of the petals and crimson purple on the petals in the center of the bloom with vinous red at the outer surface edges. This plant has a vigorous growth habit and a good aptitude for forcing, especially in the summer, and is not particularly affected by the cryptomatic diseases. Also, all parts of the plants of this variety are likely to serve for reproduction purposes.

I claim:

1. A new and distinct rose plant of the hybrid tea class, substantially as herein shown and described, particularly distinguished by its large double red flowers, a vigorous growth habit and a good aptitude for forcing.

* * * * *